United States Patent [19]
Thomas

[11] Patent Number: 5,603,794
[45] Date of Patent: Feb. 18, 1997

[54] METHOD FOR MANUFACTURING ANGLED TAPE TABS FOR USE WITH DISPOSABLE ABSORBENT ARTICLES

[75] Inventor: Suzanne M. Thomas, Fairfield, Ohio

[73] Assignee: The Procter & Gamble Company, Cincinnati, Ohio

[21] Appl. No.: 605,413

[22] Filed: Feb. 22, 1996

[51] Int. Cl.[6] .............................. A61F 13/15; A61F 13/58
[52] U.S. Cl. ........................ 156/256; 156/264; 156/289; 156/66; 604/389; 604/390; 604/391
[58] Field of Search ...................................... 156/289, 256, 156/264, 269, 66; 604/386, 387, 390, 389, 391

[56] References Cited

U.S. PATENT DOCUMENTS

| | | | |
|---|---|---|---|
| 3,610,244 | 10/1971 | Jones, Sr. ................ | 604/390 |
| 3,862,834 | 1/1975 | Small . | |
| 3,893,460 | 7/1975 | Karami . | |
| 3,897,293 | 7/1975 | Babcock . | |
| 4,001,072 | 1/1977 | de Neui .............................. | 604/389 X |
| 4,025,373 | 5/1974 | Hirsch et al. ....................... | 604/390 X |
| 4,144,887 | 3/1979 | Milnamow . | |
| 4,209,016 | 6/1980 | Schaar ................... | 604/390 |
| 4,491,493 | 1/1985 | Eaton . | |
| 4,531,992 | 7/1985 | Eaton . | |
| 4,576,600 | 3/1986 | Joa ........................ | 604/390 |
| 5,004,630 | 4/1991 | Polski . | |
| 5,021,111 | 6/1991 | Swenson . | |
| 5,106,384 | 4/1992 | Polski . | |
| 5,264,264 | 11/1993 | Shibata et al. . | |
| 5,288,546 | 2/1994 | Roessler et al. . | |
| 5,342,685 | 8/1994 | Gobran . | |
| 5,399,177 | 3/1995 | Blaney et al. . | |
| 5,399,219 | 3/1995 | Roessler et al. . | |
| 5,482,588 | 1/1996 | Goulait et al. . | |
| 5,487,809 | 1/1996 | Goulait et al. . | |

FOREIGN PATENT DOCUMENTS 4-226183  8/1992  Japan .
93/22996  11/1993  WIPO .

Primary Examiner—Jeff H. Aftergut
Attorney, Agent, or Firm—Kevin C. Johnson; Steven W. Miller; Jacobus C. Rasser

[57] ABSTRACT

A method for the manufacture of angled tape tabs for use with disposable absorbent articles. The first step is to provide an adhesive coated substrate having a first centerline and a second centerline perpendicular to the first centerline. A release substrate having a release surface and an adhesive surface is contacted with the adhesive coated substrate and partially covers the adhesive coated substrate to form a laminate. The laminate is then cut at an angle to the first centerline to form individual angled tape tabs. Each angled tape tab has a fixed end and a refastenable end. The fixed end of the angled tape tab is then secured to an absorbent article.

21 Claims, 6 Drawing Sheets

5,603,794

METHOD FOR MANUFACTURING ANGLED TAPE TABS FOR USE WITH DISPOSABLE ABSORBENT ARTICLES

FIELD OF THE INVENTION

The present invention relates to a method for manufacturing and securing tape tabs to disposable absorbent articles, and more particularly to a method for manufacturing and securing angled tape tabs to disposable absorbent articles.

BACKGROUND OF THE INVENTION

The use of adhesive tape fastener systems for securing the corners of a disposable absorbent article such as a diaper is well known in the art. Examples of these types of adhesive tape fastener systems are described in U.S. Pat. No. Re. 26,151 entitled "Disposable Diaper" which issued to Robert C. Duncan et al. on Jan. 31, 1967; and U.S. Pat. No. 3,848,594 entitled "Tape Fastening Systems for Disposable Diaper" which issued to Kenneth B. Buell on Nov. 19, 1974.

Adhesive tape fastener systems provide a secure means for keeping a disposable absorbent article on the wearer during use. In addition, refastenable adhesive tape fastener systems allow the disposable absorbent article to be folded or rolled up into a tight package for disposal, secured in the disposable configuration, and easily disposed in waste receptacles.

Mechanical fastening systems also provide a secure means for keeping a disposable absorbent article on the wearer during use. In addition, mechanical fastening systems are generally viewed as being an improvement to adhesive tape fastener systems because mechanical fastening systems are not contaminated by oils and powders, are generally considered more convenient to refasten than adhesive tape fastening systems, and do not cause the backsheet of the absorbent article to rip or tear when the fastening system is unfastened as sometimes is the case with adhesive fastening systems. An example of a mechanical fastening system is described in U.S. Pat. No. 4,963,140 entitled "Mechanical Fastening Systems With Disposal Means For Disposable Absorbent Articles" which issued to Robertson et al. on Oct. 16, 1990.

Both adhesive tape fastening systems and mechanical fastening systems employ a closure member and a landing member. Typically, the closure member is disposed adjacent the longitudinal edge of the body portion in either the front or rear of the absorbent article waist regions. Generally, the closure members are aligned such that they are placed on the disposable absorbent article parallel to the machine direction during manufacture. However, it has been found that it may be advantageous to place the closure members on the absorbent articles at an angle to the machine direction or longitudinal centerline of the disposable diaper to provide improved fit and containment about the wearer's waist. Thus, it would be advantageous to provide a simple and convenient method for manufacturing angled tabs for disposable absorbent articles.

SUMMARY OF THE INVENTION

The present invention provides a method for the manufacture of angled tabs for use with disposable absorbent articles. The first step is to provide a substrate having a first centerline and a second centerline perpendicular to the first centerline. The substrate is then cut at an angle to the first centerline to form individual angled tabs. Each angled tab has a fixed end and a refastenable end. The fixed end of the angled tab is then secured to an absorbent article.

In another embodiment, the present invention provides a method for manufacturing an angled tape tab for use with a disposable diaper. The first step is to provide an adhesive coated substrate having a first centerline and a second centerline perpendicular to the first centerline. A release substrate having a release surface and an adhesive surface is contacted with the adhesive coated substrate and partially covers the adhesive coated substrate to form a laminate. The laminate is then cut at an angle to the first centerline to form individual angled tape tabs. Each angled tape tab has a fixed end and a refastenable end. The fixed end of the angled tape tab is then secured to the disposable diaper. Preferably, the fixed end of the angled tape tab is secured to the backsheet of the disposable diaper. Alternatively, the fixed end of the angled tape tab may be secured to the topsheet, or between the topsheet and the backsheet.

BRIEF DESCRIPTION OF THE DRAWINGS

While the specification concludes with claims particularly pointing out and distinctly claiming the subject matter which is regarded as the present invention, it is believed that the invention will be better understood from the following description which is taken in conjunction with the accompanying drawings, in which:

DETAILED DESCRIPTION OF THE INVENTION

The method of the present invention is particularly suitable for manufacturing angled tape tabs for use with disposable absorbent articles. As used herein, the term "absorbent article" refers to devices which absorb and contain body exudates, and more specifically, refers to devices which are placed against the skin of a wearer to absorb and contain the various exudates discharged from the body. The term "disposable" is used herein to describe absorbent articles which are not intended to be laundered or otherwise restored or reused as an absorbent article after a single use (i.e. they are intended to be discarded, and preferably, recycled, composted or otherwise disposed of in an environmentally compatible manner). A "unitary" absorbent article refers to an absorbent article which is formed from separate parts united together to form a coordinated entity so that they do not require separate manipulative parts like a separate holder and liner. A preferred embodiment of a unitary absorbent article comprising angled tape tabs manufactured by the method of the present invention is the disposable absorbent article shown in FIG. 1. As used herein, the term "diaper" refers to an absorbent article generally worn by infants and incontinent persons that is generally worn about the lower torso of the wearer. It should be understood, however, that the present invention is also applicable to other absorbent articles such as incontinence briefs, diaper holders, feminine hygiene garments, training pants, and the like.

Figure 1:
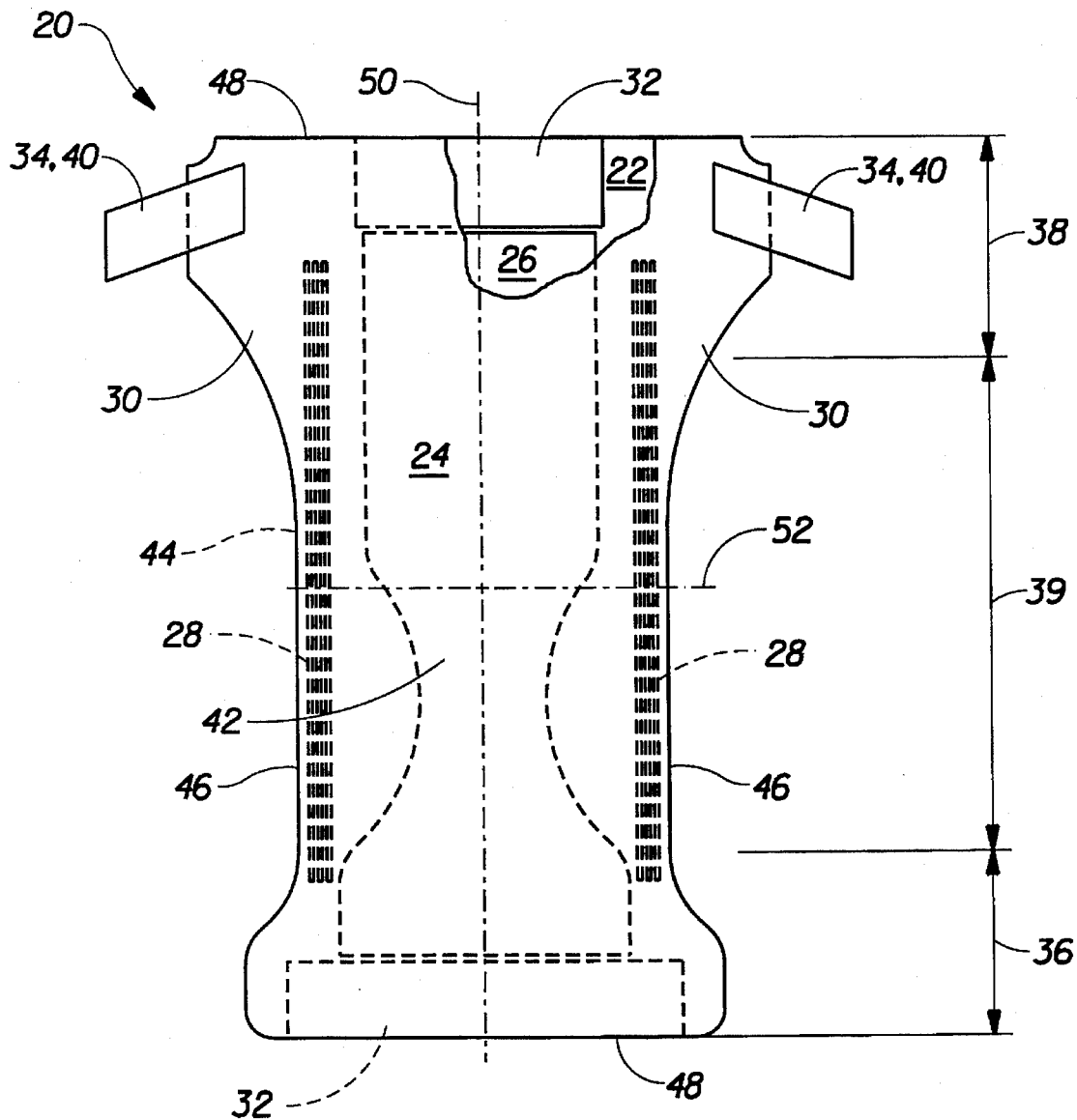
FIG. 1 is a plan view of an absorbent article comprising an angled tape tab manufactured in accordance with the method of the present invention.

With reference to FIG. 1, an absorbent article, such as diaper 20, generally comprises a liquid pervious topsheet 22, a liquid impervious backsheet 24 joined to the topsheet 22, and an absorbent core 26 positioned between the topsheet 22 and the backsheet 24. The diaper 20 preferably further comprises elasticized leg cuffs 28, ear flaps 30, an elastic waist feature 32 and a fastening system 34 comprising at least one angled tape tab 40.

The diaper 20 is shown in FIG. 1 to have an outer surface 42 (facing the viewer in FIG. 1), an inner surface 44 opposed to the outer surface 42, a front waist region 36, a rear waist region 38 opposed to the front waist region 36, a crotch region 39 positioned between the front waist region 36 and the rear waist region 38, and a periphery which is defined by the outer perimeter or edges of the diaper in which the longitudinal edges are designated 46 and the end edges are designated 48. The inner surface 44 of the diaper 20 comprises that portion of the diaper 20 which is positioned adjacent to the wearer's body during use (i.e., the inner surface 44 generally is formed by at least a portion of the topsheet 22 and other components joined to the topsheet 22). The outer surface 42 comprises that portion of the diaper 20 which is positioned away from the wearer's body (i.e., the outer surface 42 is generally formed by at least a portion of the backsheet 24 and other components joined to the backsheet 24). As used herein, the term "joined" encompasses configurations whereby an element is directly secured to the other element by affixing the element directly to the other element, and configurations whereby the element is indirectly secured to the other element by affixing the element to intermediate member(s) which in turn are fixed to the other element. The front waist region 36 and the rear waist region 38 extend from the end edges 48 of the periphery to the crotch region 39.

The diaper 20 also has two centerlines, a longitudinal centerline 50 and a transverse centerline 52. The term "longitudinal", as used herein, refers to a line, axis, or direction in the plane of the diaper 20 that is generally aligned with (e.g., approximately parallel with) a vertical plane which bisects a standing wearer into left and right halves when the diaper 20 is worn. The terms "transverse" and "lateral", as used herein, are interchangeable and refer to a line, axis or direction which lies within the plane of the diaper which is generally perpendicular to the longitudinal direction (which divides the wearer into front and back body halves).

FIG. 1 shows a preferred embodiment of the diaper 20 in which the topsheet 22 and the backsheet 24 have length and width dimensions generally larger than those of the absorbent core 26. While the topsheet 22, backsheet 24, and the absorbent core 26 may be assembled in a variety of well-known configurations, an example of a preferred absorbent article to which the tape tabs of the present invention may be joined is more fully and completely described in U.S. Pat. No. 5,151,092 entitled "Absorbent Article With Dynamic Elastic Waist Feature Having A Predisposed Resilient Flexural Hinge", issued to Buell et al. on Sep. 29, 1992 which is hereby incorporated by reference herein.

Figure 2:
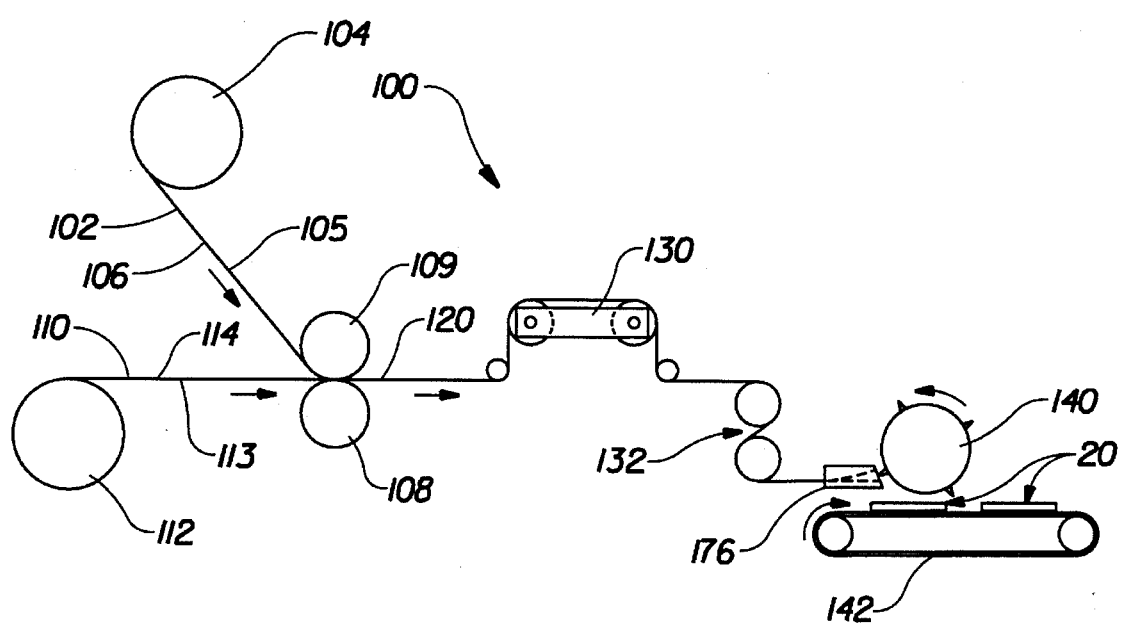
FIG. 2 is a representative side view of the method for manufacturing an angled tape tabs of the present invention.

Referring now to FIG. 2, there is shown a method and apparatus for manufacturing and securing an angled tape tab to an absorbent article, such as a disposable diaper. Examining apparatus 100 in greater detail, an adhesive coated substrate 102 is provided and taken from the unwind roll 104. The adhesive coated substrate 102 has a backing surface 105 and an adhesive surface 106. The adhesive coated substrate 102 may comprise any adhesive coated material commonly used for tape tabs on absorbent articles. In a preferred embodiment, the adhesive coated substrate 104 comprises a polyolefin or a polyester film ranging in thickness from about 2.5 mils to about 5.0 mils in thickness, more preferably about 4 mils in thickness.

As shown in FIG. 2, the adhesive coated substrate 102 is taken from the unwind roll 104 and is fed toward combining rolls 108 and 109. A release substrate 110 having a release surface 114 and an adhesive surface 113 is taken from the unwind roll 112. The release substrate 110 is fed toward combining rolls 108 and 109 where it is combined with adhesive coated substrate 102. The release substrate is narrower in width than the adhesive coated substrate and therefore only partially covers the adhesive coated substrate 102 to form a laminate 120. As seen in FIG. 2, the release surface 114 of the release substrate 110 is secured to the adhesive surface 106 of the adhesive coated substrate 102.

The laminate 120 then preferably passes through a tracking system 130 as is commonly utilized and known in the art to track and adjust the laminate 120 into the S-wrap tensioning rolls 132. A tracking system manufactured by the Fife Corporation of Oklahoma City, Okla., and sold as Model Op6 LRA may be suitable. The S-wrap tensioning rolls 132 provide proper tensioning to prevent puckering or bunching of the laminate 120.

Figure 3:
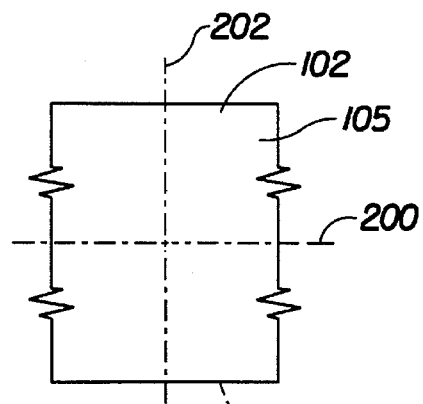
FIG. 3 is a greatly enlarged view showing the adhesive coated substrate prior to being combined with the release agent.

The laminate 120 is then directed to a taper unit 140. The taper unit 140 cuts the laminate at an angle to form individual angled tape tabs and joins the individual angled tape tabs to an absorbent article. Preferably, the angled tape tabs are secured to the backsheet portion of diaper 20 which is being carried by conveyor 142. FIG. 3 is a greatly enlarged view showing, the adhesive coated substrate 102 prior to being combined with the release substrate 110. As described above, the angled tape tabs 40 of the present invention are made by first providing an adhesive coated substrate 102. FIG. 3 shows the adhesive coated substrate 102 having a first centerline 200 and a second centerline 202 perpendicular to the first centerline 200. As used herein, the term "first centerline" refers to an imaginary line that runs parallel to the machine direction. As used herein, the term "second centerline" refers to an imaginary line that runs perpendicular to the machine direction and parallel to the cross-machine direction. The adhesive coated substrate 102 further comprises a backing surface 105 and an adhesive surface 106 opposed to the backing surface 105.

Figure 4:
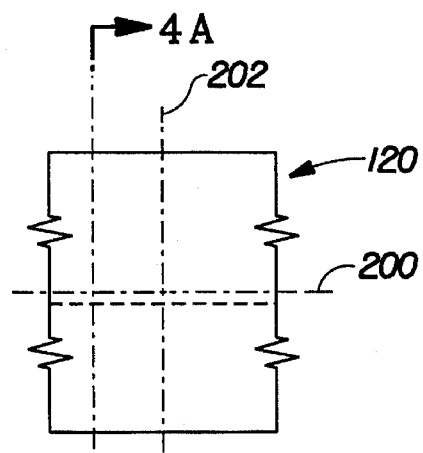
FIG. 4 is a greatly enlarged view showing the laminate after passing through the combining rolls.
Figure 4A:
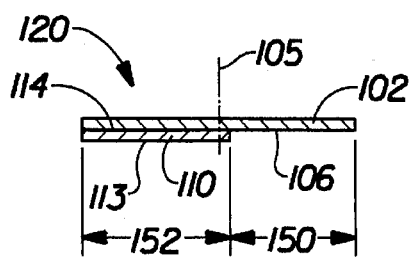
FIG. 4A is a cross-sectional view of the laminate of FIG. 4 taken along section line 4A—4A of FIG. 4.

FIG. 4 is a greatly enlarge view showing the laminate 120 after passing through combining rolls 108 and 109. Referring now to FIG. 4A there is shown a cross-sectional view of the laminate 120 taken along section line 4A—4A of FIG. 4. The laminate 120 comprises the adhesive coated substrate 102 secured to the release substrate 110. The release substrate 110 has an adhesive surface 113 and a release surface 114 opposed to the adhesive surface 113. As shown in FIG. 4A the release surface 114 of the release substrate 110 is secured to the adhesive surface 106 of the adhesive coated substrate 102. Since the release substrate 110 is narrower in width (i.e., in the transverse or cross-machine direction 202) than the adhesive coated substrate 102, the release substrate 110 only partially covers the adhesive coated substrate 102. The laminate 120 has a fixed region 150 and a refastenable region 152. The portion of the adhesive coated substrate 102 partially covered by the release substrate 110 forms the refastenable region 152. The uncovered portion of the adhesive coated substrate forms the fixed region 150 of the laminate. The fixed region 150 will be the portion of the angled tape tab that becomes fixedly secured to the disposable diaper 20.

Figure 5:
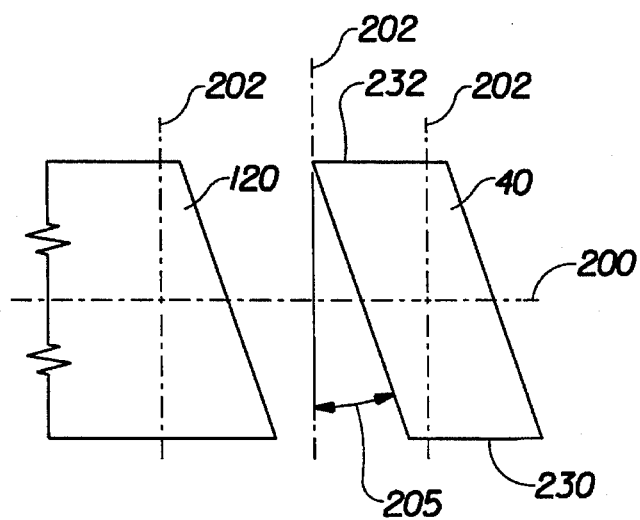
FIG. 5 is a greatly enlarged view of the laminate after having been cut into individual angled tape tabs.

FIG. 5 is a greatly enlarged view of the laminate after having been cut by taper unit 140. The tape unit 140 cuts the laminate 120 at an angle to the first centerline 200 to form individual angled tape tabs 40. The laminate 120 is cut at an angle indicated as 205 in FIG. 5. Angle 205 is preferably from about 2° to about 40°, and more preferably from about 10° to about 30°, and most preferably from about 15° to about 25°.

Figure 6:
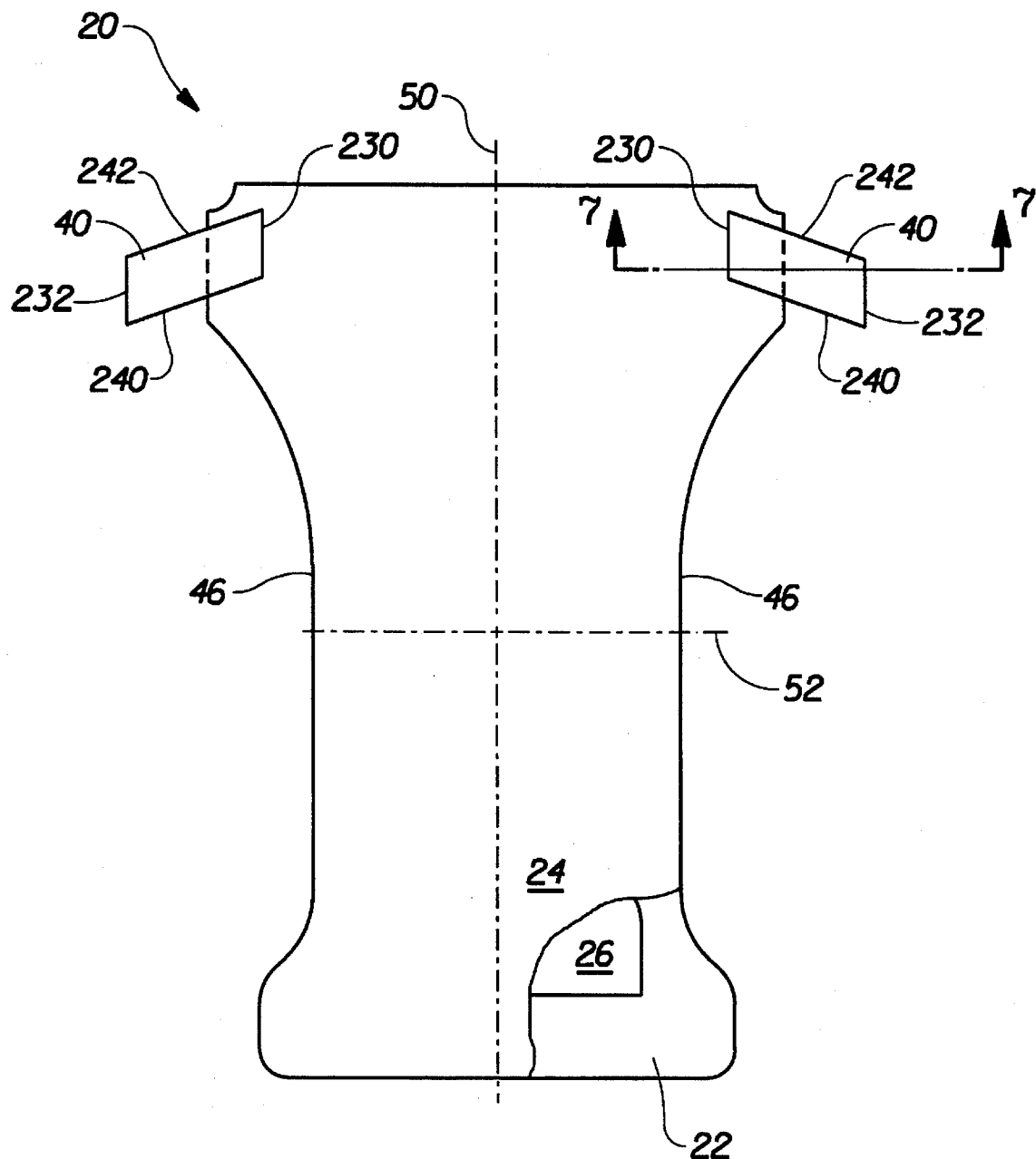
FIG. 6 is a plan view of a diaper comprising the angled tape tab manufactured in accordance with the method of the present invention.

Referring now to FIG. 6 there is shown an angled tape tab 40 secured to a disposable diaper 20 comprising a topsheet 22, a backsheet 24 joined to the topsheet 22 and an absorbent core 26 positioned between the topsheet 22 and the backsheet 24. As shown in FIG. 6 the angled tape tabs 40 extend at an angle to the longitudinal centerline 50 of the disposable diaper 20. Each angled tape tab 40 has a first longitudinal edge 230 and a second longitudinal edge 232. The first and second longitudinal edges 230 and 232 respectively, are aligned essentially parallel to the longitudinal centerline 50 of the disposable diaper 20. The angled tape tabs 40 further comprise a first angled edge 240 and a second angled edge 242. The first and second angled edges 240 and 242, respectively, are not aligned either parallel to the longitudinal centerline 50 or the transverse centerline 52 of the disposable diaper 20.

Figure 7:
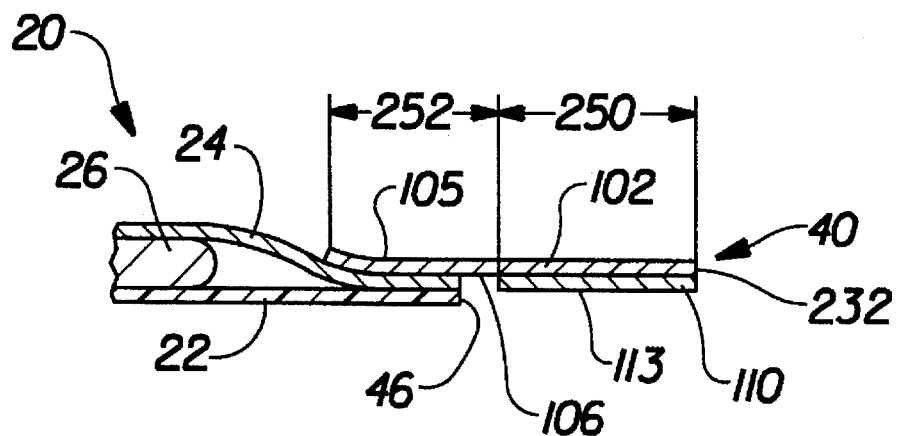
FIG. 7 is a cross-sectional view of the diaper of FIG. 6 taken along section line 7—7.

Referring now to FIG. 7 there is shown a cross-sectional view of the diaper 20 of FIG. 6 taken along section line 7—7. Each individual angled tape tab 40 has a fixed end 252 and a refastenable end 250. The fixed end 252 of the tape tab 40 may be joined to the topsheet 22 or the backsheet 24 of the disposable diaper 20. Further, the fixed end 252 may be joined between the topsheet 22 and the backsheet 24, or to any other element of the disposable diaper 20. In the embodiment shown in FIG. 7, the fixed end 252 is joined to the backsheet 24 of the disposable diaper 20. In particular, the adhesive surface 106 of the fixed end 252 is secured to the diaper backsheet 24.

Figure 8:
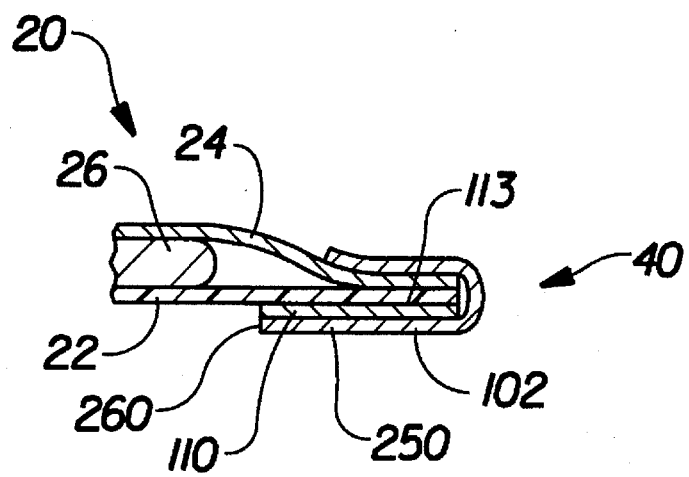
FIG. 8 is a cross-section view of the diaper after the tape tab has been folded to fixedly secure the release substrate to the diaper topsheet.

Referring now to FIG. 8 the tape tab 40 is shown after having been folded to fixedly secure the adhesive surface 113 of the release substrate 110 to the topsheet 22. From this configuration, a user will be able to grasp the refastenable end 250 of the tape tab separating the adhesive coated substrate 102 from the release substrate 110 and open the tape tab 40. The end edge 260 of the adhesive coated substrate 102 may be folded inward upon itself to provide the user with a portion without adhesive thereon making the tape tab easier to grasp and open for the user. In addition, the end edge 260 may be provided with rounded corners to eliminate the possibility of harsh corner edges contacting the wearer's skin so as to prevent redmarking.

The release portion of the substrate 110 allows the refastenable portion 250 to be inwardly folded during manufacture to protect the adhesive on the adhesive coated substrate 102 from contamination or delamination prior to use.

Referring again to FIG. 2, the laminate 120 may be subjected to bending at anvil 176 prior to being cut at taper unit 140. Preferably, the laminate 120 is subjected to bending along its first centerline 200 to create a "V" shape. The "V" shape helps to stiffen the laminate 120 enabling it to withstand the forces subjected by the taper unit 140.

Figure 9:
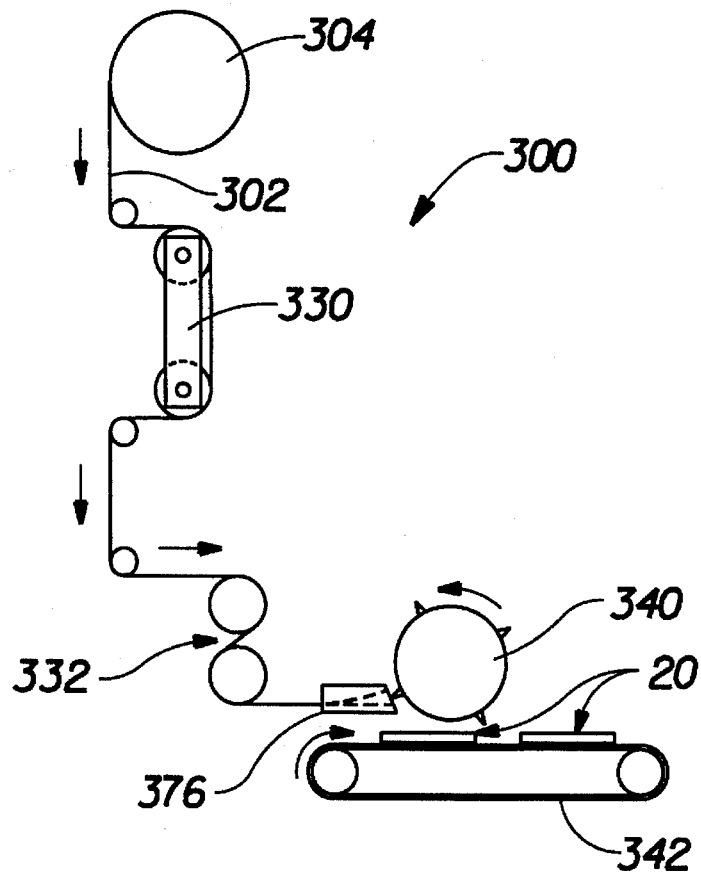
FIG. 9 is a representation side view of another method for manufacturing an angled tab of the present invention.
Figure 10:
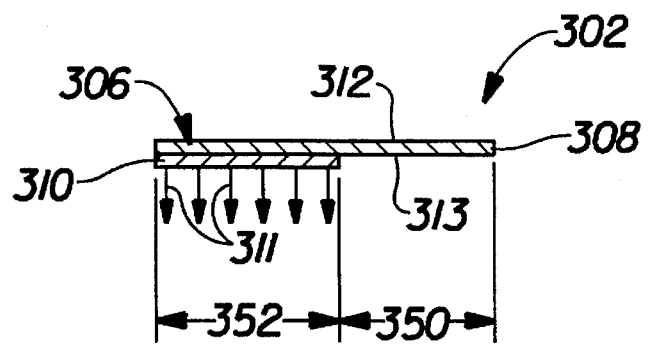
FIG. 10 is a cross-sectional view of an alternative substrate embodiment of the present invention.

Referring now to FIG. 9 there is shown another method and apparatus for manufacturing and securing an angled tab to an absorbent article, such as a disposable diaper. Examining apparatus 300 in greater detail a substrate 302 is provided and taken from the unwind roll 304. The substrate 302 is preferably a laminate comprising an adhesive coated substrate partially covered by a release substrate. A suitable substrate is laminate 120 shown in FIGS. 4 and 4A. Alternatively, substrate 302 may comprise the laminate 306 shown in FIG. 10. Laminate 306 comprises an adhesively coated substrate 308 and a mechanical fastening element such as hook fastening material 310. A suitable hook fastening material is disclosed in U.S. Pat. No. 4,963,140 issued to Robertson et al. on Oct. 16, 1990 which patent is incorporated herein by reference. The adhesively coated substrate 308 has a backing surface 312 and an adhesive surface 313. As seen in FIG. 10, the hook fastening material is narrower in width than the adhesive coated substrate and therefore only partially covers the adhesive coated substrate. The hook fastening material 310 comprising hooks 311 is secured to the adhesive surface 313 of the adhesive coated substrate 308.

The substrate 302 has a first centerline and a second centerline perpendicular to the first centerline. The first centerline runs parallel to the machine direction while the second centerline runs perpendicular to the machine direction and parallel to the cross-machine direction.

The substrate 302 then preferably passes through a tracking system 330 as is commonly utilized and known in the art to track and adjust the substrate 302 into the S-wrapped tensioning rolls 332. The S-wrapped tensioning roll 332 provide proper tensioning to prevent puckering or bunching of the substrate 302. The substrate 302 is then subjected to bending at anvil 376 prior to being cut at taper unit 340. The substrate 302 is then directed to a taper unit 340 which cuts the substrate 302 at an angle to the first centerline to form individual angled tabs and joins the individual angled tabs to an absorbent article such as disposable diaper 20. Preferably, the angled tabs are secured to the backsheet portion of the diaper 20 which is being carried by conveyor 342.

Referring again to FIG. 10 since the hook fastening material 310 is narrower in width than the adhesive coated substrate 308, the hook fastening material 310 only partially covers the adhesive coated substrate 308. The laminate 306 has a fixed region 350 and a refastenable region 352. The portion of the adhesive coated substrate 308 partially covered by the hook fastening material 310 forms the refastenable region 352 while the uncovered portion of the adhesive coated substrate 308 forms the fixed region 350. The fixed region 350 is the portion of the angled tab that is fixedly secured to the backsheet of the disposable diaper 20.

In an alternative embodiment of the present invention, an angled tape tab is first secured to a substrate which is then cut and secured to an absorbent article. A substrate having a first centerline and a second centerline perpendicular to the first centerline is provided. The substrate is then cut at an angle to the first centerline to form individual angled tape tabs. The individual angled tape tabs are then joined to a second web or substrate, such as a substrate which will form the side panels or ears of the diaper. The second substrate having the angled tape tabs joined thereto is then cut preferably along the second centerline to form individual side panels. The individual side panels are then joined to the disposable diaper.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for manufacturing an angled tape tab for a disposable absorbent article, comprising the steps of:

providing an adhesive coated substrate having a first centerline and a second centerline perpendicular to said first centerline;

contacting a release substrate having a release surface and an adhesive surface with said adhesive coated substrate such that said release substrate partially covers said adhesive coated substrate to form a laminate;

cutting said laminate at an angle to the first centerline to form individual angled tape tabs, each angled tape tab having a fixed end and a refastenable end; and securing said fixed end of said angled tape tab to an absorbent article comprising a topsheet and a backsheet.

2. The method of claim 1 wherein said adhesive coated substrate has a backing surface and an adhesive surface opposed to said backing surface.

3. The method of claim 2 wherein said release surface of said release substrate contacts the adhesive surface of said adhesive coated substrate.

4. The method of claim 1 further comprising the step of folding said angled tape tab to secure said release substrate to said absorbent article.

5. The method of claim 4 wherein said release substrate is secured to said topsheet.

6. The method of claim 1 wherein said fixed end of said angled tape tab is secured to said backsheet.

7. The method of claim 1 further comprising the step of bending said laminate prior to being cut.

8. The method of claim 1 wherein said absorbent article comprises a disposable diaper.

9. A method for manufacturing an angled tape tab for a disposable diaper, comprising the steps of:

providing an adhesive coated substrate having a backing surface, an adhesive surface opposed to said backing surface, a first centerline and a second centerline perpendicular to said first centerline;

contacting a release substrate having a release surface and an adhesive surface with said adhesive coated substrate such that said release substrate partially covers said adhesive coated substrate to form a laminate;

cutting said laminate at an angle to the first centerline to form individual angled tape tabs, each angled tape tab having a fixed end and a refastenable end; and securing said fixed end of said angled tape tab to a disposable diaper.

10. The method of claim 9 wherein said disposable diaper comprises a topsheet, a backsheet joined to said topsheet, and an absorbent core positioned between said topsheet and said backsheet.

11. The method of claim 10 wherein said fixed end of said angled tape tab is secured to said backsheet.

12. The method of claim 9 wherein said release surface of said release substrate contacts the adhesive surface of said adhesive coated substrate.

13. The method of claim 9 further comprising the step of folding said angled tape tab to secure said release substrate to said absorbent article.

14. The method of claim 13 wherein said release substrate is secured to said topsheet.

15. The method of claim 9 further comprising the step of bending said laminate prior to being cut.

16. A method for manufacturing an angled tab for a disposable absorbent article, comprising the steps of:

providing a substrate having a first centerline and a second centerline perpendicular to said first centerline;

cutting said substrate at an angle to the first centerline to form individual angled tabs, each angled tab having a fixed end and a refastenable end; and securing said fixed end of said angled tab to an absorbent article comprising a topsheet and a backsheet.

17. The method of claim 16 wherein said substrate is an adhesive coated substrate having a backing surface and an adhesive surface opposed to said backing surface.

18. The method of claim 17 further comprising the step of contacting a release substrate having a release surface and an adhesive surface with said adhesive coated substrate.

19. The method of claim 16 wherein said substrate comprises a hook fastening material.

20. The method of claim 16 wherein said fixed end of said angled tab is secured to said topsheet.

21. The method of claim 16 wherein said fixed end of said angled tab is secured to said backsheet.

* * * * *